(12) United States Patent
Johnson

(10) Patent No.: US 7,213,477 B2
(45) Date of Patent: May 8, 2007

(54) QUICK DISCONNECT INTERFACE FOR ENVIRONMENTAL TESTING

(75) Inventor: Edward A. Johnson, Terre Haute, IN (US)

(73) Assignee: TRW Automotive U.S. LLC, Livonia, MI (US)

( * ) Notice: Subject to any disclaimer, the term of this patent is extended or adjusted under 35 U.S.C. 154(b) by 98 days.

(21) Appl. No.: 11/032,947

(22) Filed: Jan. 11, 2005

(65) Prior Publication Data
US 2006/0150755 A1    Jul. 13, 2006

(51) Int. Cl.
*G01N 17/00*    (2006.01)
*G01K 17/00*    (2006.01)

(52) U.S. Cl. .................. 73/865.6; 702/136; 374/57
(58) Field of Classification Search ............. 73/865.6; 702/136, 130, 132, 763, 765, 555; 324/760, 324/73.1; 374/57, 50
See application file for complete search history.

(56) References Cited

U.S. PATENT DOCUMENTS

| | | | |
|---|---|---|---|
| 4,949,031 A * | 8/1990 | Szasz et al. ............... 324/537 |
| 5,929,340 A | 7/1999 | Cochran et al. ............ 73/766 |
| 6,005,404 A | 12/1999 | Cochran et al. ............ 324/760 |
| 6,313,652 B1 * | 11/2001 | Maeng ...................... 324/760 |
| 6,373,270 B1 | 4/2002 | Cochran et al. ............ 324/760 |
| 6,564,165 B1 | 5/2003 | Mailloux et al. ........... 702/136 |

FOREIGN PATENT DOCUMENTS

JP    2004212091 A    *    7/2004

\* cited by examiner

*Primary Examiner*—Hezron Williams
*Assistant Examiner*—Tamiko Bellamy
(74) *Attorney, Agent, or Firm*—Tarolli, Sundheim, Covell & Tummino LLP

(57) ABSTRACT

An apparatus (10) tests different products (15). The apparatus (10) includes an environmental chamber (20) for providing thermal shock to the products (15), a conveyor (40) for transporting the products (15) through the environmental chamber (20), a fixture (100) movable with the products (15) through the environmental chamber (15), and an interface (300) removably mounted on the fixture (100). The fixture (100) has a means (60, 80) for electric stimulation and monitoring of the products (15) during transport of the products (15) through the environmental chamber (20). The interface (300) is constructed to test one of the different products. The interface (300) provides a mechanical and electrical connection between the fixture (100) and the product being tested. The interface (300) is tailored for stimulating and monitoring the product being tested.

27 Claims, 4 Drawing Sheets

QUICK DISCONNECT INTERFACE FOR ENVIRONMENTAL TESTING

TECHNICAL FIELD

The present invention relates to the testing of electrical components, and more particularly, relates to thermal shock testing of electrical components.

DESCRIPTION OF THE PRIOR ART

Electrical components are commonly tested at high and low temperatures to identify which components would not operate effectively at high and low temperatures. A conventional testing procedure is a batch process. In a batch process a number of electrical components are simultaneously heated and cooled as a group and monitored as a group.

Also, an in-line testing process is known. In an in-line process, the electrical components are moved sequentially through a tunnel having a cold chamber portion and a hot chamber portion. The electrical components are monitored as they move sequentially through the tunnel. The monitoring determines which components are not operative through a temperature range, in which the components are intended to operate. Thus, the monitoring determines which components are defective.

In an in-line process, a conveyor system transports electronic components through discrete electrical test stations in spaced apart hot and cold zones. The components are electrically tested at the electrical test stations at predetermined locations in the hot and cold zones.

SUMMARY OF THE INVENTION

An apparatus in accordance with one aspect of the present invention tests products. The apparatus includes an environmental chamber for providing thermal shock to the products, a conveyor for transporting the products through the environmental chamber, a fixture movable with the products through the environmental chamber, and an interface removably mounted on the fixture. The fixture has a means for electric stimulation and monitoring of the products during transport of the products through the environmental chamber. The interface is constructed to test one of the different products. The interface provides a mechanical and electrical connection between the fixture and the product being tested. The interface is tailored for stimulating and monitoring the product being tested.

A method in accordance with another aspect of the present invention tests a first product and a second product. The method includes the steps of: mounting the first product on a first interface having a first set of pin probes specifically tailored for stimulating and monitoring the first product; mounting the interface and first product on a fixture; maintaining the interface and fixture in an environmental chamber; electrically stimulating the first product through the first set of pin probes during said maintaining step; monitoring the effect of the stimulating step on the first product; removing the interface and first product from the fixture; mounting the second product on a second interface having a second set of pin probes for stimulating and monitoring the second product; mounting the second interface and second product on the fixture; maintaining the second interface and fixture in the environmental chamber; electrically stimulating the second product through the second set of pin probes during the second maintaining step; and monitoring the effect of said second stimulating step on the second product.

An apparatus in accordance with still another aspect of the present invention tests a product. The apparatus includes an environmental chamber for providing thermal shock to the product, a conveyor for transporting the product through the environmental chamber, a fixture movable with the product through the environmental chamber, and an interface removably mounted on the fixture. The fixture has a means for electric stimulation and monitoring of the product during transport of the product through the environmental chamber. The interface provides a mechanical and electrical connection between the fixture and the product. The interface is tailored for stimulating and monitoring the product. The interface includes a pivotal press down plate for securing the product to the interface and ensuring electrical contact between circuitry on the product and electrical probes of the interface. The interface further includes a fixture latch for securing the press down plate during transport of the product through the environmental chamber.

BRIEF DESCRIPTION OF THE DRAWINGS

The foregoing and other features of the present invention will become apparent to those skilled in the art to which the present invention relates upon reading the following description with reference to the accompanying drawings, wherein.

DESCRIPTION OF A PREFERRED EMBODIMENT

Figure 1:
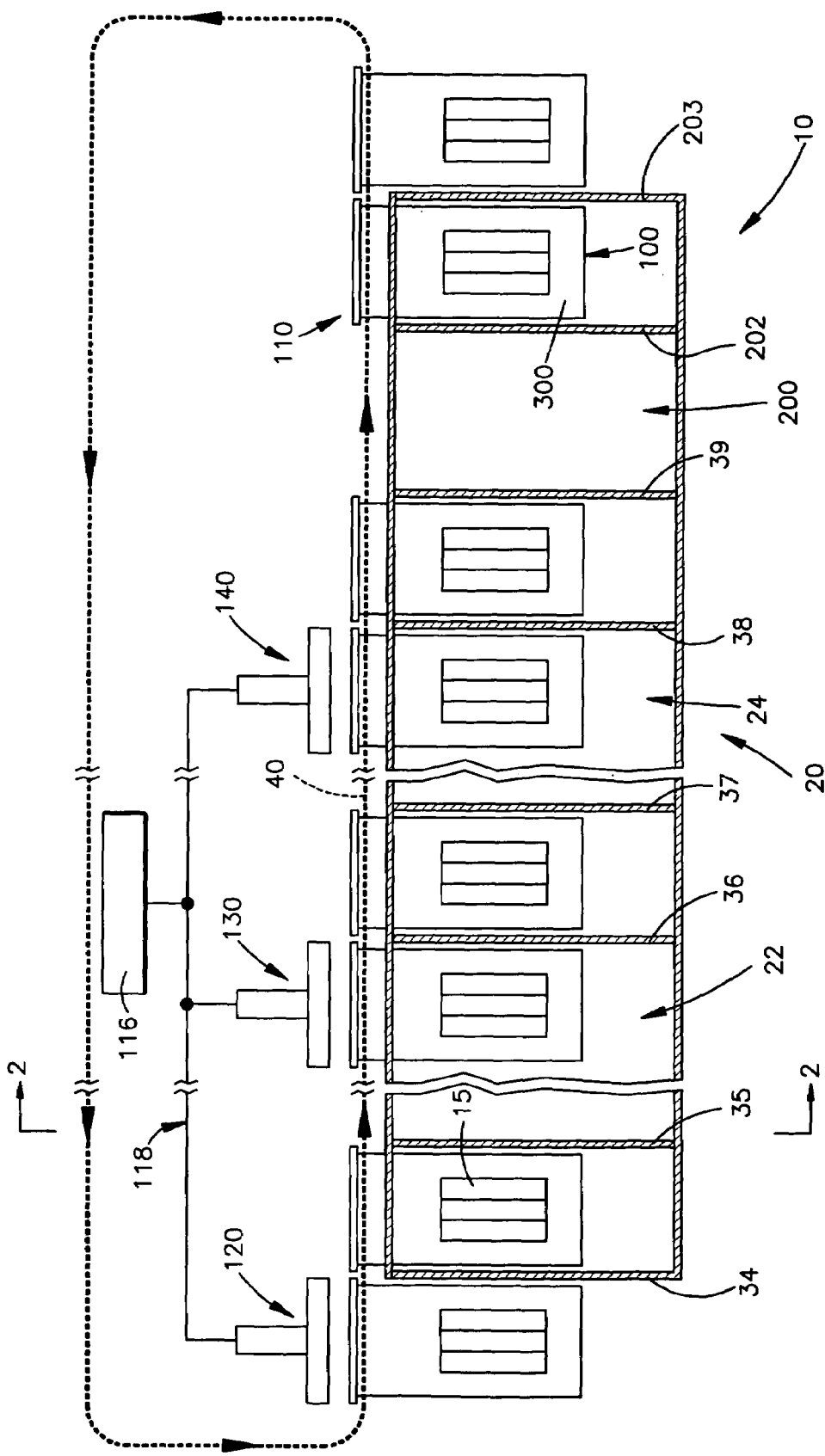
FIG. 1 is a schematic view of an apparatus embodying the present invention.

As representative of the present invention, FIG. 1 illustrates an apparatus 10 for inline testing of a product 15. The product 15 may be an airbag crash sensor and control unit, an anti-lock brake module, a traction control module, or similar electronic device. The apparatus 10 applies to product specific test tooling and electrical testing of the products 15 for use in assemblies such as anti-lock brake systems, vehicle stability control systems, traction control systems, airbag systems, remote acceleration systems, etc.

Figure 2:
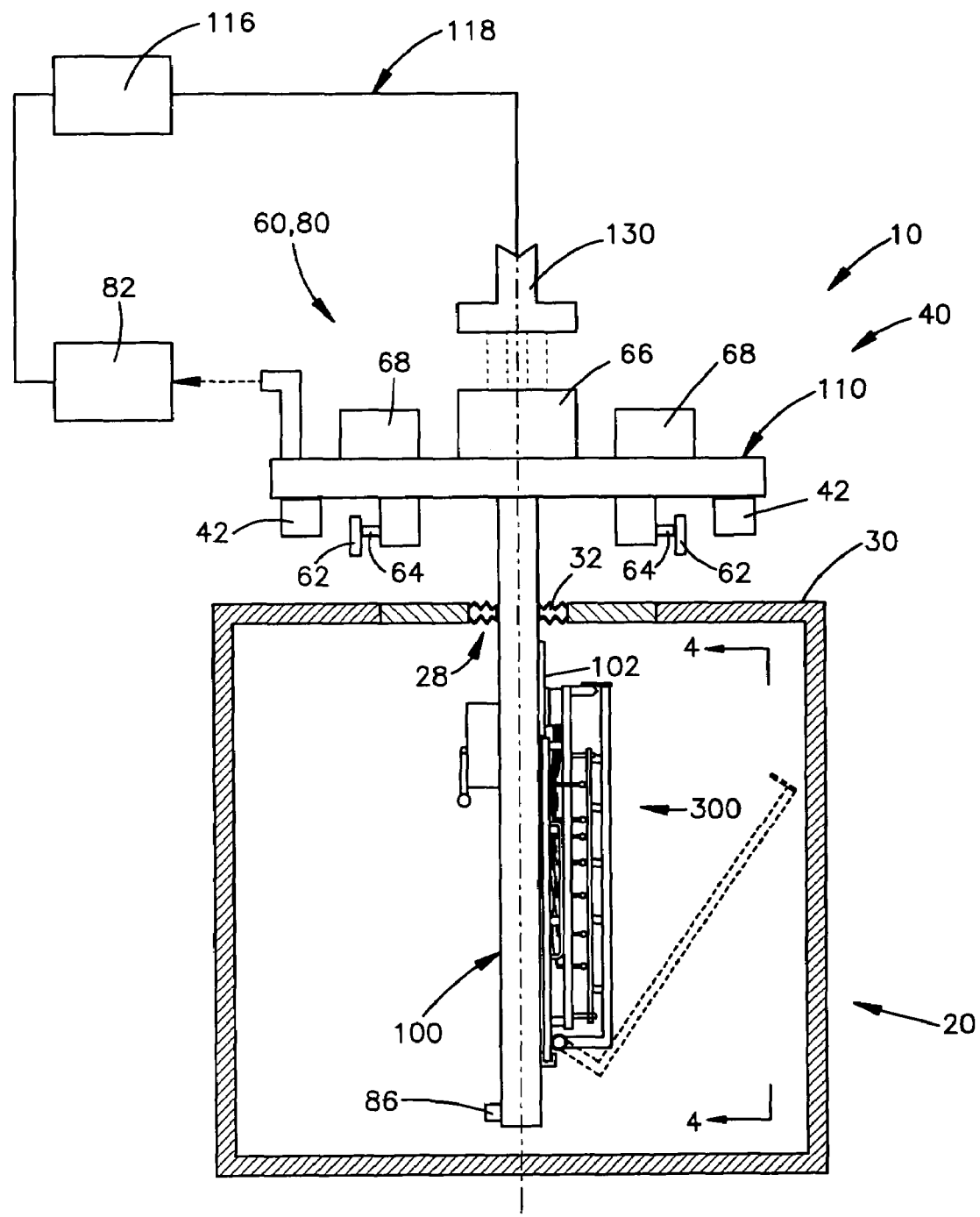
FIG. 2 is a schematic sectional view along line 2—2 in FIG. 1.

The apparatus 10 includes an environmental chamber 20, a conveyor 40, a stimulation means 60 (FIG. 2), and a monitoring means 80 (FIG. 2). The environment chamber 20 is a box-like enclosure through which the products 15 are sequentially moved by the conveyor 40. The environmental chamber has an entrance door 34 which is movable to an open position to enable products 15 to enter the chamber 20 and a closed position to enclose the products 15 within the chamber 20.

The environmental chamber 20 is about 40 feet long but may be a different length depending on the product being tested. The environmental chamber 20 includes a hot zone 22 and a cold zone 24. The hot zone 22 typically ranges in temperature from 85° C. to 125° C. The cold zone 24 is typically −40° C. The temperature of the hot zone 22 and cold zone 24 can vary depending upon design criteria of the products 15.

The products 15 are mounted on a vertical fixture 100 prior to being conveyed through the chamber 20. The fixture is connected to a horizontal pallet 110. The fixture 100 and pallet 110 are hard wired together and plug into each other. The pallet 110 is conveyed outside the chamber 20 by the conveyor 40 while the fixture 100 is moved through the chamber 20. The pallet 110 and fixture 100 have a length as measured in the direction of conveyor travel of about 18 inches, but this length could be some other dimension.

The environmental chamber 20 has an elongate slot 28 (FIG. 2) in its upper surface 30 for allowing the fixture 100 to extend into and travel through the environmental chamber 20 and still be in contact with, and hard-wired to, the pallet 110 located above the environmental chamber 20. The slot 28 may have a flexible, elastomeric material 32 lining the slot 28 for thermally resisting heat transfer around the fixture 100. The pallet 110 and fixture 100 form a T-shaped structure (FIG. 2) with the fixture 100 forming the lower, vertical part of the "T" and extending down through the slot 28 and into the environmental chamber 20.

Typically, three electronic components are attached to the fixture 100 at any one time for simultaneous testing of each component which are the products 15 being tested. The conveyor 40, located above the environmental chamber 20, transports the products 15 through the hot 22 and cold 24 zones of the environmental chamber 20. The conveyor 40 includes two belts 42 (FIG. 2) on which the pallet 110 rests. The two belts 42 travel above the environmental chamber 20 and frictionally engage the pallet 110, thereby moving the pallet 110 along the upper surface 30 above the environmental chamber 20. The conveyor 40 moves in incremental steps (typically 20 inches) at predetermined time intervals (typically 90 seconds). Thus, the conveyor 40 moves, and then is stationary for a time interval (90 seconds), and then moves again.

This incremental movement of the conveyor 40 allows a plurality of pallets/fixtures 100, 110 (typically 18 inches in length) to be spaced apart by the 20 inch incremental steps and to travel through the environmental chamber 20 simultaneously, but at different stages of the overall test process, as shown in FIG. 1. The stimulation means 60 provides cyclic electric stimulation of the products 15 during transport of the products 15 through the environmental chamber 20. Two buss bars 62 are located between the two belts 42 of the conveyor 40 and provide electronic power to the pallet 110 through spring loaded brushes 64 located on the pallet 110.

Typically, multiple brushes are connected in parallel. This configuration maintains a constant power supply to the pallet 110, even when one or more connections at the buss bar/brush interfaces are temporarily broken by the sliding of the spring loaded brushes 64 against the buss bars 62.

A master microprocessor 66 and a plurality of slave microprocessors 68 (typically one for each product 15) comprise the stimulating means 60. The master microprocessor 66 and the slave microprocessors 68 are located on the pallet 110. Each slave microprocessor 68 controls the testing, or stimulating, of each product 15. The master microprocessor 66 controls the operation and functioning of the slave microprocessors 68. The location of the master 66 and slave 68 microprocessors above the environmental chamber 20 on the pallet 110 allows them to remain at ambient temperature throughout the test process, thereby maximizing their functional lives.

The monitoring means 80 monitors the effect of the stimulation means 60 on the products 15 during transport of the products 15 through the environmental chamber 20 and throughout the temperature transitions incurred by the products 15. The monitoring means 80 includes the master microprocessor 66, infrared links 82, and a plurality of test heads 120, 130, 140 which periodically engage an interface assembly (not shown) on the pallet 110 and perform additional data collection and testing.

The master microprocessor 66 records performance data of each product 15 (i.e., pass/fail) during their travel through the environmental chamber 20 in its memory. Some components fail at extreme temperatures and then "heal" as the temperature of the component is returned from that extreme temperature. After this healing, the component appears fully functional in all respects. However, the component has a much shorter functional life. Consequently, the monitoring by the master microprocessor 66 allows detection of this type of failure before "healing" can occur.

Additionally, mechanical connection failures, or fixturing failures, may occur during temperature transitions as each product 15 travels through the environmental chamber 20. In this type of failure, parts of the products 15 may become detached and then reattached. These "intermittent" failures are largely independent of extreme temperature and mainly occur during temperature transitions due to various temperature gradients incurred by the products 15. The monitoring by the master microprocessor 66 allows detection of this type of failure before reattachment can occur.

The fixture 100 has a feedthru printed circuit board (PCB) 102 providing communication with the pallet 110. The feedthru PCB 102 is mounted on one side of the vertical fixture 100 (FIG. 2). The feedthru PCB 102 includes custom electrical circuitry on a printed circuit board assembly. This circuitry has connectors that interface with the pallet 110 and a fixture input/output connector 104 mounted on the feedthru PCB 102.

A connector seat/unseat mechanism 106 is mounted on the vertical side of the fixture 100 opposite the feedthru PCB 102. The connector seat/unseat mechanism 106 provides for a quick connect/disconnect of an electrical and mechanical interface 300 (described below).

Figure 4:
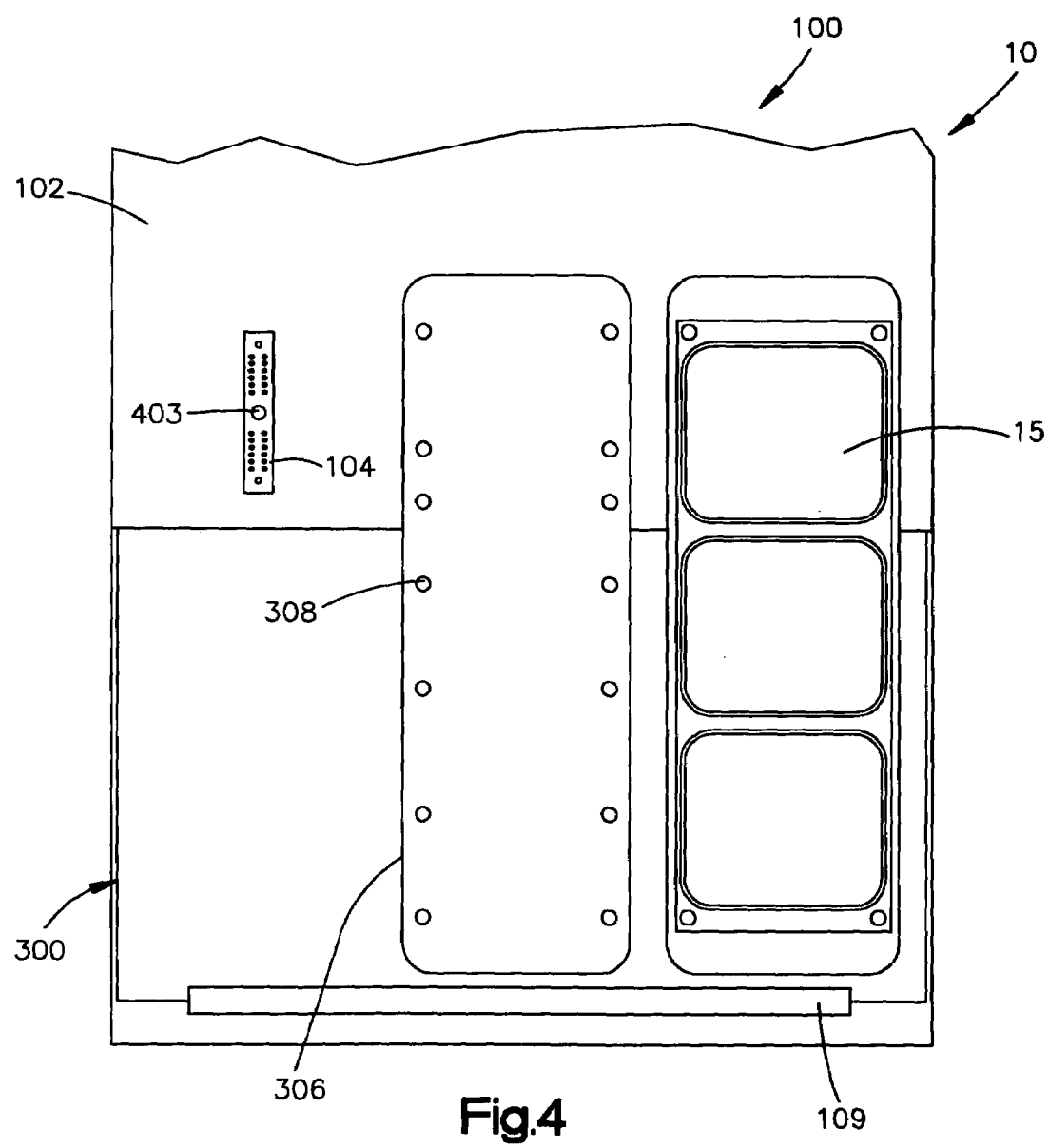
FIG. 4 is schematic sectional view along line 4—4 in FIG. 2.

The fixture input/output connector 104 carries electrical signals between the feedthru PCB 102 and the products 15. The flat, vertical fixture 100 further has a horizontally extending ledge 109 for supporting the interface 300 mounted on the fixture. The ledge 109 is located along the bottom edge of the fixture 100 (FIG. 4). The interface 300 is supported by the ledge 109 when the interface is mounted on the fixture 100 (FIG. 2).

The connector seat/unseat mechanism 106 causes the three fixture input/output connectors 104 to each engage or disengage with a corresponding connector 108 mounted on the interface 300. The connector seat/unseat mechanism 106 includes a handle 401 and three tooling pins 403. The tooling pins 403 extend through the fixture 100 from the handle 401.

Figure 3:
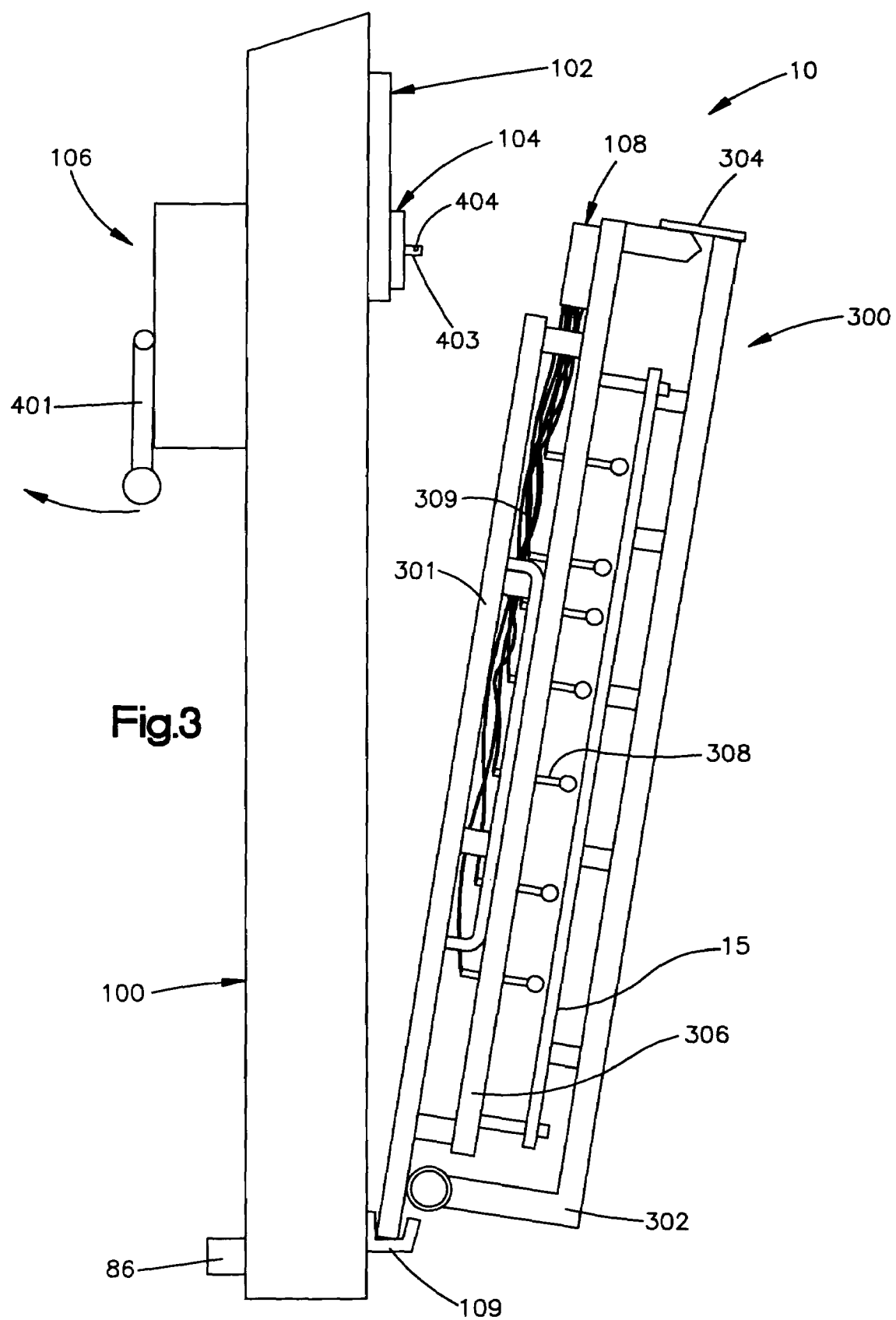
FIG. 3 is a schematic detail view of part of FIG. 2.

Each tooling pin 403 has a helical groove 404 (FIG. 3) that engages the interface 300 and secures the interface to the fixture 100 so that the three fixture input/output connectors 104 are properly aligned with the corresponding connectors 108 on the interface. The handle 401 is connected to a linkage (not shown) that causes the tooling pins 403 to rotate simultaneously when the handle is rotated in one direction. This rotation of the handle 401 allows the helical grooves 404 of the tooling pins 403 to engage pins (not shown) on the interface 300, similar to a threaded engagement. When the handle 401 is rotated in the opposite direction, the interface 300 is released and the interface may be replaced on the fixture 100 with another interface tailored and constructed to test a different product other than the product 15.

The interface 300 electrically interconnects the fixture 100 and the products 15. The interface 300 interconnects the circuitry of the environmental test pallet 100, 110 and the products 15 and provides a conduit for electrical stimulus and loads from the pallet 100, 110 to the products 15. The interface 300 further provides for feedback measurement of the performance of the products 15 by the components (60, 80) of the pallet 110.

The interface 300 further includes a base plate 301 and a pivotal press down plate 302 that mechanically secure the products 15 to the interface 300. The press down plate 302 also ensures electrical contact between circuitry on the products 15 and electrical probes 308 of the interface 300. A fixture latch 304 holds the press down plate 302 in place during transport of the fixture 100 through the environmental test chamber 20. Each of three product test fixtures 306 mounted on the base plate 301 of the interface 300 electrically engage a product 15 through the connectors 108 during transport of the fixture 100 through environmental test chamber 20. Conductive pin probes 308, constructed in a pattern designed for a particular product, extend through the product test fixtures 306 and make electrical contact with the circuitry on the products 15 when the products are seated in the interface 300. Wires 309 connect each pin probe 308 to one or more contacts on each fixture input/output connector 104 of the fixture 100 through each connector 108.

FIG. 4 shows part of the interface 300 installed on the fixture 100. The press down plate 302 has been removed. The left product location has no product 15 and no product test fixture 306 installed so that the tooling pin 403 is visible. The center location has a product test fixture 306 installed, but no product 15 so that the pin probes 308 are visible. The right location has a product 15 in place for testing as the interface 300 moves through the environmental chamber 20.

Conventional test pallet designs incorporate a product specific vertical test fixture attached permanently to a horizontal test pallet. This results in a test pallet and test fixture configuration dedicated to a particular product. The apparatus 10 of the present invention, specifically the interface 300, allows for the quick connect and disconnect of test circuitry from a test pallet's electrical circuits. Thus, the interface 300 allows for a reduced changeover time from one product to another, reduced costs for product specific test tooling and equipment, and reduced engineering development time for new product specific test fixtures. The interface 300 further allows for reduced storage space requirements for product specific test fixtures, increased reliability of the test pallet and fixtures thereby reducing ongoing maintenance costs, and increased serviceability of the test pallet and fixtures making it easier to perform routine maintenance and repairs.

An indexing means 86, such as a silicon chip with a temperature transducer, is located on the fixture 100 for communicating to the master microprocessor 66 the location and temperature at which failures occur. This data can be useful in determining why a defect occurred and how to correct the manufacturing or assembly process which created the defect.

The infrared links 82 are located at intervals along the upper surface 30 of the environmental chamber 20 for communicating pass/fail and other data from the pallet 110 to a central monitoring point 116, such as a computer terminal.

Typically three test heads 120, 130, 140 are utilized for a more extensive statistical analysis of the performance of the products 15 during their travel through the environmental chamber 20. After loading products 15 onto the fixture 100, a first head 120, or pretest head, is lowered into engagement with the master microprocessor 66 before the fixture 100 enters the environmental chamber 20, as shown in FIG. 1. This pretest step determines the parameters at various critical locations, known as test nodes, on each product 15. The initial ambient status of each node on each product 15 is determined and that data is transferred to the central monitoring point 116 through the master microprocessor 66, the first head 120, and a data highway 118. Initial failures may be detected here.

After the pretest step is concluded, the first head 120 is raised, a first entrance door 34 is opened, and the conveyor 40 transports the pallet 110 one incremental step above the environmental chamber 20 and the fixture 100 the same one incremental step into the environmental chamber 20. The first entrance door 34 closes and the fixture 100 remains between the first entrance door 34 and a second entrance door 35 for the predetermined time interval.

Then, the second entrance door 35 opens, the pallet/fixture 100, 110 travels one incremental step, and the fixture 100 enters the hot zone 22 with the second entrance door 35 closing behind it.

During the following incremental steps (typically 9) within the hot zone 22, the temperature of the products 15 stabilizes to the temperature of the hot zone 22. The master microprocessor 66 monitors the performance of the products 15 during this temperature transition and stabilization.

During the last incremental step in the hot zone 22, a second head 130 is lowered to engage the master microprocessor 66. The second head 130 monitors and stores the parameters at the test nodes on each product 15 during this time.

After this analysis is conducted (one predetermined time interval), the second head 130 is raised, a first intermediate door 36 opens, the pallet/fixture 100, 110 advances one incremental step, and the first intermediate door 36 closes. The fixture 100 remains between the first intermediate door 36 and a second intermediate door 37 for one predetermined time interval. During this time, the products 15 begin to cool as the temperature between the first 36 and second 37 intermediate doors fluctuates in the range between the temperature of the hot zone 22 and the temperature of the cold zone 24 (due to the opening and closing of the first 36 and second 37 intermediate doors). The master microprocessor 66 monitors the performance of the products 15 during this temperature transition period.

Then, the second intermediate door 37 opens, the pallet/fixture 100, 110 advances one incremental step into the cold zone 24, and the second intermediate door 37 closes. During the following incremental steps (typically 9) within the cold zone 24, the temperature of the products 15 stabilizes to the temperature of the cold zone 24. The master microprocessor 66 monitors the performance of the products 15 during this temperature transition and stabilization.

During the last incremental step in the cold zone 24, a third head 140 is lowered to engage the master microprocessor 66. The third head 140 monitors and stores the parameters at the test nodes on each product 15 during this time.

After this analysis is conducted (one predetermined time interval), the third head 140 is raised, a third intermediate door 38 opens, the pallet/fixture 100, 110 advances one incremental step, and the third intermediate door 38 closes. The fixture 100 remains between the third intermediate door 38 and a fourth intermediate door 39 for one predetermined time interval.

Then, the fourth intermediate door 39 opens, the fixture 100 advances one incremental step into a warm-up zone 200, and the fourth intermediate door 39 closes. During the following incremental steps (typically 9) within the warm-up zone 200, the temperature of the products 15 stabilizes to ambient temperature. After the last incremental step in the warm-up zone 200, a first exit door 202 opens, the pallet/fixture 100, 110 advances one incremental step, and the first exit door 202 closes. The fixture 100 remains between the first exit door 202 and a second exit door 203 for one predetermined time interval. Then, the second exit door 203 opens, the fixture 100 advances one incremental step out of the warm-up zone 200, and the second exit door 203 closes. The products 15 may now be disconnected and unloaded from the interface 300 of the fixture 100 and routed appropriately, as determined by the above analyses.

The interface 300 may also be quickly disconnected from the fixture 100 utilizing the connector seat/unseat mechanism 106. Another interface tailored to another test product may be secured to the fixture 100 at this time.

The above inline testing may be conducted in conjunction with a Computer Integrated Manufacturing (CIM) program. Using the real time feedback available by this testing apparatus/method, virtually immediate correction of manufacturing and assembly errors can be realized. The waste incurred by the production of a multitude of defect components, caused by the time lag for discovery of the origins of the defect, can be greatly reduced by the apparatus/method of the present invention.

From the above description of the invention, those skilled in the art will perceive improvements, changes and modifications. Such improvements, changes and modifications within the skill of the art are intended to be covered by the appended claims.

Having described the invention, the following is claimed:

1. An apparatus for inline testing of different products, said apparatus comprising:
   an environmental chamber for providing thermal shock to the products;
   a conveyor for transporting the products through said environmental chamber;
   a fixture movable with the products through said environmental chamber, said fixture having a means for electric stimulation and monitoring of the products during transport of the products through said environmental chamber; and
   an interface removably mounted on said fixture and being constructed to test one of the different products, said interface providing a mechanical and electrical connection between said fixture and the one product being tested, said interface being tailored for stimulating and monitoring the one product being tested.

2. The apparatus as set forth in claim 1 wherein said interface includes a pivotal press down plate for securing the products to said interface.

3. The apparatus as set forth in claim 1 wherein said interface includes a press down plate for ensuring electrical contact between circuitry on the products and-electrical probes of said interface.

4. The apparatus as set forth in claim 1 wherein said interface includes a fixture latch for securing a press down plate during transport of the products through said environmental chamber.

5. The apparatus as set forth in claim 1 wherein said interface includes a product test fixture for electrically engaging a product during transport of the particular product through said environmental chamber.

6. The apparatus as set forth in claim 1 wherein said interface includes conductive pin probes for electrically contacting a product when the product is secured in said interface.

7. The apparatus as set forth in claim 1 wherein said interface includes a wire for connecting a pin probe of said interface to a contact on said fixture.

8. The apparatus as set forth in claim 1 further including another interface for replacing said interface, said other interface being removably mounted on said fixture and being tailored for stimulating and monitoring another product.

9. The apparatus as set forth in claim 1 further including a pallet for supporting said fixture during transport of the products through said environmental chamber.

10. The apparatus as set forth in claim 1 further including a buss bar and a brush for providing continuous electrical power to said fixture during transport of the products through said environmental chamber.

11. A method for inline testing of a first product and a second product, said method comprising the steps of:
   mounting the first product on a first interface having a first set of pin probes specifically tailored for stimulating and monitoring the first product;
   mounting the interface and first product on a fixture;
   maintaining the interface and fixture in an environmental chamber;
   electrically stimulating the first product through the first set of pin probes during said maintaining step;
   monitoring the effect of said stimulating step on the first product;
   removing the interface and first product from the fixture;
   mounting the second product on a second interface having a second set of pin probes for stimulating and monitoring the second product;
   mounting the second interface and second product on the fixture;
   maintaining the second interface and fixture in the environmental chamber;
   electrically stimulating the second product through the second set of pin probes during said second maintaining step;
   monitoring the effect of said second stimulating step on the second product.

12. The method as set forth in claim 11 further including the step of securing the first set of pin probes of the first interface against predetermined locations on the first product by a pivotal press down plate.

13. A method for inline testing of a first product and a second product, said method comprising the steps of:
   mounting the first product on a first interface having a first set of pin probes specifically tailored for stimulating and monitoring the first product;
   mounting the interface and first product on a fixture;
   maintaining the interface and fixture in an environmental chamber;
   electrically stimulating the first product through the first set of pin probes during said maintaining step;
   monitoring the effect of said stimulating step on the first product;
   removing the interface and first product from the fixture;
   mounting the second product on a second interface having a second set of pin probes for stimulating and monitoring the second product;
   mounting the second interface and second product on the fixture;
   maintaining the second interface and fixture in the environmental chamber;
   electrically stimulating the second product through the second set of pin probes during said second maintaining step;

monitoring the effect of said second stimulating step on the second product; and wherein said removing step includes rotating a tooling pin for releasing the first interface from the fixture.

14. The method as set forth in claim 11 wherein said first maintaining step includes maintaining the fixture and first product in a hot zone and, subsequently, maintaining the fixture and first product in a cold zone.

15. The method as set forth in claim 11 further including the step of interconnecting an environmental test pallet outside of the environmental chamber with the first product through the first interface.

16. An apparatus for inline testing of a product, said apparatus comprising:
   an environmental chamber for providing thermal shock to the product;
   a conveyor for transporting the product through said environmental chamber;
   a fixture for moving with the product through said environmental chamber, said fixture having a means for electric stimulation and monitoring of the product during transport of the product through said environmental chamber; and
   an interface removably mounted on said fixture, said interface providing a mechanical and electrical connection between said fixture and the product, said interface being tailored for stimulating and monitoring the product, said interface including a pivotal press down plate for securing the product to said interface and ensuring electrical contact between circuitry on the product and electrical probes of said interface, said interface further including a fixture latch for securing said press down plate during transport of the product through said environmental chamber.

17. The apparatus as set forth in claim 16 further including another interface for replacing said interface, said other interface being removably mounted on said fixture and being tailored for stimulating and monitoring another product.

18. The apparatus as set forth in claim 17 further including a pallet for supporting said fixture during transport of the product through said environmental chamber, said pallet remaining outside of said environmental chamber during transport of the product through said environmental chamber.

19. The apparatus as set forth in claim 18 further including a buss bar and a brush for providing continuous electrical power to said fixture through said pallet during transport of the product through said environmental chamber.

20. The apparatus as set forth in claim 1 wherein said fixture includes a ledge for supporting the interface mounted on said fixture.

21. The apparatus as set forth in claim 20 wherein said ledge is located along the bottom edge of the fixture and extends substantially horizontal.

22. The apparatus as set forth in claim 1 including a connector mechanism operatively associated with said fixture and said interface, said connector mechanism being operable to cause said interface to be connected to said fixture, said connector mechanism being operable to cause said interface to be disconnected from said fixture.

23. The apparatus as set forth in claim 22 wherein said connector mechanism includes a handle, said handle being movable in a direction to cause said interface to be connected to said fixture, said handle being movable in the opposite direction to cause said interface to be disconnected from said fixture.

24. The apparatus as set forth in claim 23 wherein said connector mechanism includes at least one tooling pin, said tooling pin being rotatable by said handle in a direction to connect said tooling pin to said interface such that said interface is connected to said fixture, said tooling pin being rotatable by said handle in the opposite direction to disconnect said tooling pin from said interface such that said interface is disconnected from said fixture.

25. The apparatus as set forth in claim 22 wherein said connector mechanism includes at least one tooling pin, said tooling pin being rotatable in a direction to connect said tooling pin to said interface such that said interface is connected to said fixture, said tooling pin being rotatable in the opposite direction to disconnect said tooling pin from said interface such that said interface is disconnected from said fixture.

26. The method as set forth in claim 11 wherein the second interface and second product are mounted at the same location as that of the first interface and first product.

27. The method as set forth in claim 11 wherein the first and second interfaces are different.

* * * * *